(12) United States Patent
Shin et al.

(10) Patent No.: US 9,731,063 B2
(45) Date of Patent: Aug. 15, 2017

(54) PORTABLE FUNCTIONAL APPARATUS FOR CLEANING VAGINA

(76) Inventors: Mi Chong Shin, Seoul (KR); In Sung Shin, Goyang-Si (KR)

( * ) Notice: Subject to any disclaimer, the term of this patent is extended or adjusted under 35 U.S.C. 154(b) by 786 days.

(21) Appl. No.: 14/352,102

(22) PCT Filed: Dec. 12, 2011

(86) PCT No.: PCT/KR2011/009528
§ 371 (c)(1),
(2), (4) Date: Apr. 16, 2014

(87) PCT Pub. No.: WO2013/058436
PCT Pub. Date: Apr. 25, 2013

(65) Prior Publication Data
US 2014/0276429 A1    Sep. 18, 2014

(30) Foreign Application Priority Data

Oct. 18, 2011 (KR) ...................... 10-2011-00106607

(51) Int. Cl.
*A61M 3/02*        (2006.01)
*A61H 19/00*       (2006.01)
(Continued)

(52) U.S. Cl.
CPC .......... *A61M 3/0258* (2013.01); *A61F 5/455* (2013.01); *A61H 19/44* (2013.01); *A61H 23/0263* (2013.01); *A61H 35/00* (2013.01); *A61M 3/02* (2013.01); *A61M 3/0279* (2013.01); *A61F 5/4553* (2013.01); *A61H 2205/087* (2013.01);
(Continued)

(58) Field of Classification Search
CPC ............ A61M 2210/1475; A61F 5/455; A61F 5/4553
See application file for complete search history.

(56) References Cited

U.S. PATENT DOCUMENTS

| 4,405,321 A * | 9/1983 | Budoff | ................ A61M 3/0262 604/212 |
| 5,858,010 A * | 1/1999 | Berry  | .................. A61M 3/0262 222/568 |

(Continued)

FOREIGN PATENT DOCUMENTS

| KR | 10-2005-0076335 | 7/2005 |
| KR | 10-2006-0097261 | 9/2006 |

(Continued)

*Primary Examiner* — Bhisma Mehta
*Assistant Examiner* — William Frehe
(74) *Attorney, Agent, or Firm* — Lex IP Meister, PLLC.

(57) ABSTRACT

A portable functional vaginal cleansing apparatus is provided to prevent inflammation in vagina, to maintain cleanness, and to enhance massage effect. A portable functional vaginal cleansing apparatus comprises: a doughnut-shaped main body; a semicylinder water tank with a water level indicator (100) on the outside and a coupling protrusion inside; a handle part (380) with a coupling groove mounted at the coupling protrusion; a pumping unit (210) with a motor and a pump; and a control unit (290) with a rotator which is formed to rotate within a predetermined range, a insertion protrusion connected to a hose, an insertion unit with a nozzle part, an on and off switch, a water level controller, and an operation lamp.

6 Claims, 5 Drawing Sheets

(51) Int. Cl.
    *A61H 23/02*     (2006.01)
    *A61H 35/00*     (2006.01)
    *A61F 5/455*     (2006.01)

(52) U.S. Cl.
    CPC ............... *A61M 2202/0468* (2013.01); *A61M 2210/1475* (2013.01)

(56) References Cited

U.S. PATENT DOCUMENTS

| | | | |
|---|---|---|---|
| 6,379,341 B1* | 4/2002 | Cho | A61M 3/0262 604/142 |
| 6,752,792 B1* | 6/2004 | Robertson | A61M 3/0258 4/443 |
| 2002/0055723 A1* | 5/2002 | Liu | A61M 3/0262 604/279 |
| 2014/0012191 A1* | 1/2014 | Iparraguirre | A61M 3/0262 604/87 |

FOREIGN PATENT DOCUMENTS

| | | |
|---|---|---|
| KR | 10-2006-0114662 | 11/2006 |
| KR | 10-1007-8270000 | 1/2011 |

* cited by examiner

PORTABLE FUNCTIONAL APPARATUS FOR CLEANING VAGINA

TECHNICAL FIELD

The present invention relates to a portable functional apparatus for cleaning a vagina, and more particularly to an apparatus with convenient portability that may clean women, prevent inflammation in a vagina from being occurred, and improve a massage effect.

BACKGROUND ART

Up to now, when keeping all of cleaning water, an injector, and a long nozzle in a small cleaning water barrel, since the long nozzle cannot be put in the small cleaning water barrel together with the injector, the cleaning water is inevitably kept separately from a female vagina cleaning device. Accordingly, each time the female vagina cleaning device is used, the vagina cleaning device should be inconveniently disinfected and the women cannot simply carry the female vagina cleaning device.

In order to solve the above problems, a long hole is formed in a center of a cleaning rod of an inner barrel in the injector in the form of a tunnel and a nozzle keeping chamber in which the nozzle may be put is made. Upon keeping the female vagina cleaning device, after the cleaning water and the injector are simultaneously put in the small cleaning water barrel and the nozzle is put in a nozzle keeping chamber for the cleaning rod of an inner barrel in the injector, if a user closes a cap for a cleaning water barrel, the user may simply carry the cleaning water barrel with the cleaning water and the injector therein. Since the cleaning water in the cleaning water barrel always disinfects the injector and the nozzle, the user can directly utilize the female vagina cleaning device regardless of time and location.

Further, as a background art of the present invention, a portable device for cleaning female secret parts is disclosed in Korean Patent No. 10-0634839. According to Korean Patent No. 10-0634839, women inconveniently use and carry the portable cleaning device. That is, since the woman sits on the portable cleaning device after the portable cleaning device is put in a separate auxiliary barrel so that cleaning is performed, it is difficult for the women to use the portable cleaning device and it is difficult to fit a nozzle of the portable cleaning device in a vagina hole.

DISCLOSURE

Technical Problem

The present invention has been made keeping in mind the above problems occurring in a device for cleaning vagina and massage of Korean Patent No. 10-1007827 issued by the applicant of the present invention, and an object of the present invention is to provide a portable functional apparatus for cleaning a vagina with convenient operational scheme and manufacture which has a handle that allows a user to use the portable functional apparatus, to hold the portable function apparatus by a hand to directly insert the portable functional apparatus in a vagina input port, and including a water barrel and a pumping part configured in an assembling scheme.

It is another object of the present invention to provide a functional apparatus for cleaning a vagina and message having a changeable donut shape that allows a user to conveniently use the functional apparatus.

Technical Solution

According to the embodiment, there is provided a portable functional apparatus for cleaning a vagina, including: a body having a donut shape; a water barrel part having a semi-cylindrical shape formed so that the body is separated by units, the water barrel part being separated from the body, and a coupling projection being formed at an inner surface of the water barrel part, a water level indicator part being formed at an outer surface of the water barrel part, a handle part formed therein with a coupling groove which is formed at the coupling projection; a pumping part coupled with the water barrel part having a semi-cylindrical shape, a hose being inserted into and coupled with an adhesion projection to exhaust a cleaning solution of the water barrel part, and the pumping part being mounted therein with a motor and a pump; and a nozzle operation part including a rotating part and a controller, the rotating part coupled with the pumping part to be rotated within a predetermined range, and a controller mounted therein with a rotating part, the controller being formed therein with a fitting projection connected to a hose to supply a cleaning solution, the controller being formed therein with an insertion hole, a nozzle part is formed in a front direction of the insertion hole, an on/off switch, a water press pressure meter, and an operation lamp being formed at an inner surface of the controller, wherein the apparatus has a projected structure inserted into the vagina, the nozzle operation part is rotated so that a nozzle part is mounted to exhaust water.

Advantageous Effects

The present invention allows a user to simply carry and use the portable functional apparatus regardless of time and location so that the user leads a healthy social life by preventing anxiety of women and providing convenience of a life.

Further, the present invention can prevent diseases from being transmitted by cleanly managing female secret parts and allows a user to give birth to a healthy baby after pregnant, and provide a portable cleaning tool capable of assisting the cure of a disease associated with the secret parts generated after the user gives birth to the baby.

BEST MODE

Mode for Invention

Figure 1:
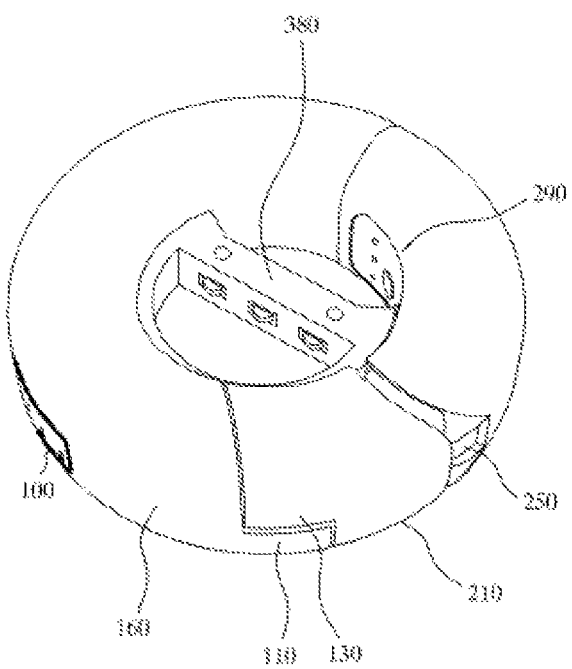
FIG. 1 is a perspective view illustrating a portable functional apparatus for cleaning a vagina according to an exemplary embodiment of the present invention.
Figure 2:
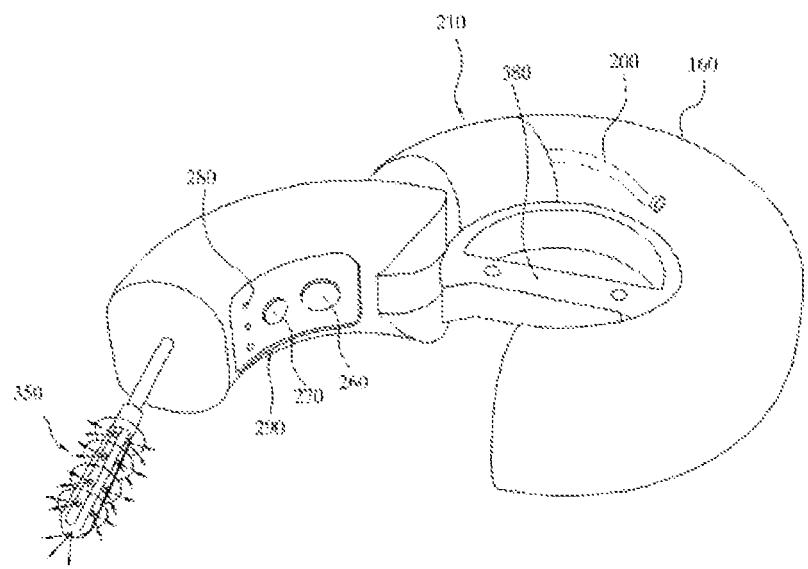
FIG. 2 is a view illustrating an operation state of the portable functional apparatus for cleaning a vagina according to an exemplary embodiment of the present invention.

Hereinafter, a portable functional apparatus for cleansing a vagina according to the exemplary embodiment of the present invention will be described with reference to the accompanying drawings.

A concept of a toilet and a bathroom is combined. With settlement of a toilet culture, interest in a health is increased regardless of age or sex. Accordingly, a device for cleaning secret parts to cleanly manage an anus and secret parts which are an important part of a body and should be clean for an easy function is increasingly spotlighted.

A device for cleaning secret parts called a bidet installed at home or indoor may represent a cleaning effect and may prevent constipation and piles which may be generated because an anus and secret parts are not clean. Since the device for cleaning secret parts is used for curing piles disease in adults of 50% but many users utilize the cleaning device, the user does not like the cleaning device. Since a cleaning solution is declined through a nozzle mounted at a toilet stool so that cleaning is performed, that is, the cleaning is achieved by only declining power of the cleaning solution, a cleaning effect is low so that women do not like to use the cleaning device. In addition, it is inconvenient for women to use a device for cleaning a vagina used at a time, and cleaning is not easily achieved so that cleanse satisfaction is degraded.

As shown in FIGS. 1 to 7, the present invention relates to a device for cleaning a vagina and message. The device for cleaning a vagina and message having a projected structure is inserted into the vagina, a nozzle operation part 300 is rotated so that a nozzle part 350 may be mounted to exhaust water.

The device for cleaning a vagina and message includes a body having a donut shape, a water barrel part 150 having a semi-cylindrical shape, a handle part 380, a pumping part 210, and a nozzle operation part 300. The water barrel part 150 is formed so that the body is separated by units. The water barrel part 150 is separated from the body, and a coupling projection 140 is formed at an inner surface of the water barrel part 150. A water level indicator 100 is formed at an outer surface of the water barrel part 150. The handle part 380 is formed therein with a coupling groove 360. The coupling groove 360 is formed at the coupling projection 140. The pumping part 210 is coupled with the water barrel part 150 having the semi-cylindrical shape and a hose 200 is inserted into and coupled with an adhesion projection 130 to exhaust a cleaning solution of the water barrel part. The pumping part 210 is mounted therein with a motor 190 and a pump 180. The nozzle operation part 300 includes a rotating part 500 and a controller 290. The rotating part 500 is coupled with the pumping part 210 and is rotated within a predetermined range. The controller 290 is mounted therein with a rotating part 500. The controller 290 is formed therein with a fitting projection 230 connected to a hose 220 to supply a cleaning solution. The controller 290 is formed therein with an insertion hole 440. A nozzle part 350 is formed in a front direction of the insertion hole 440. An on/off switch 260, a water pressure meter 270, and an operation lamp 280 are formed at an inner surface of the controller 290.

If the body includes the handle part 380, the water barrel part 150, the pumping part 210, and the nozzle operation part 300, the handle part 380, the water barrel part 150, the pumping part 210, and the nozzle operation part 300 are coupled with each other so that they are separated and coupled from and with each other.

The body has a donut shape and rotates the nozzle part 350 and is provided therein with the nozzle part 350 so that the body may be changed to a structure of being inserted in the vagina. If the user holds the handle part 380, carefully inserts the nozzle part 350 in the vagina, and operates a switch of the controller 290, a cleaning solution is exhausted from the nozzle part 350.

The handle part 380 is formed therein with a through hole 370 so that the user conveniently holds the handle part 380 by the hand, and a coupling groove 360 is formed at a front surface of the handle part 380. The coupling groove 360 is coupled with and fixed to a coupling projection 140 formed at an inner surface of the water barrel part. The handle part 380 is fixed to an inner side of the water barrel part 150 which allows the user to directly feel a weight of the cleaning solution.

The water barrel part 150 has a semi-transparent structure that allows the user to view an internal cleaning solution. A positioning projection 110 is formed at a side of the water barrel part 150, and a slice projection 120 is formed at an upper surface of the positioning projection 110 so that the water barrel part 150 may be coupled with the pumping part 210. An adhesion projection 130 is formed at an upper portion of the water barrel part 150 so that the hose may be inserted into the adhesion projection 130.

The hose may be inserted into the adhesion projection 130, and a rubber packing is formed at an edge surface of the adhesion projection 130 to prevent the cleaning solution from being leaked.

The water barrel part 150 is coupled with one surface of the pumping part 210, and the nozzle operation part 300 is coupled with an opposite surface of the pumping part 210.

The motor 190 and the pump 180 are mounted at a part coupled with the water barrel part 150 so that a cleaning solution of the water barrel part may be pumped. The hose 200 and a connection hose 220 are connected to the pump 180. The pumping part 210 may be coupled with the water barrel part 150 through the positioning groove 160 and a slice groove 140 formed at an upper portion of the positioning groove 160. The slice groove 140 and the slice projection 120 are coupled with each other by pushing the slice groove 140 and the slice projection 120. In this case, the adhesion projection 130 adheres and is coupled to the adhesion hole 170.

The nozzle operation part 300 couples the pumping part 210 with the nozzle part 350, and the rotating part 520 is configured so that the nozzle operation part 300 is rotated to a predetermined angle as an x axis representing the pumping part 210.

As an embodiment, in the rotating part 520, a fitting groove 240 is formed at the nozzle operation part 300, and a locking protrusion 250 is formed along a curved surface between an end of the fitting groove 240 and a rotatable location. A fitting projection 230 having a convex input structure is formed at a center of the rotating part 520 and is inserted into and coupled with a connection hole 200.

The rotating part 500 is configured so that the nozzle operation part 300 may be rotated as an axis representing the pumping part 210. A T shaped coupling member 490 is formed at the pumping part 210 and is inserted into the fitting groove 240 of the nozzle operation part 300. The T shaped coupling member 490 inserted into the fitting groove 240 is coupled to be moved along the locking protrusion 250.

The insertion hole 440 is coupled with the nozzle operation part 300 so that a cleaning solution is exhausted through the insertion hole 440. A support member 420 is formed therein with the insertion hole 440 and a rubber ring is formed in the insertion hole 440 so that a fitting projection 230 of the nozzle part 350 is not separated.

Figure 3:
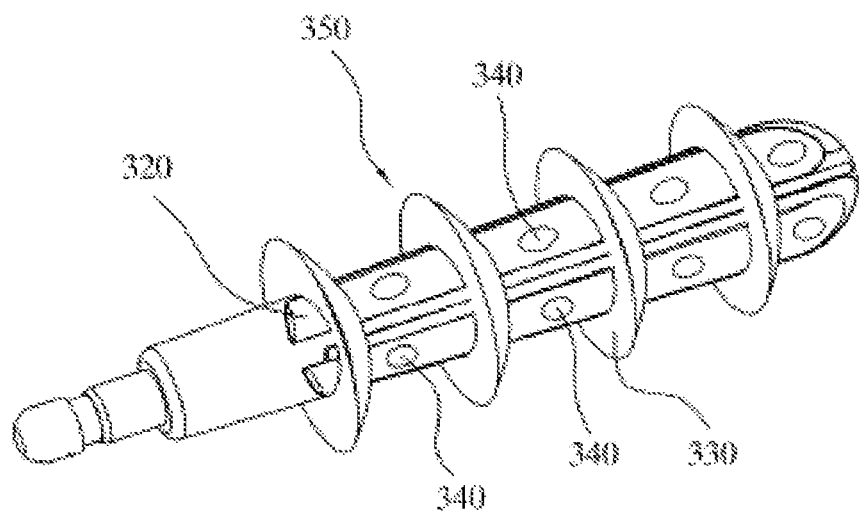
FIG. 3 is a perspective view illustrating a nozzle of the portable functional apparatus for cleaning a vagina according to an exemplary embodiment of the present invention.
Figure 4:
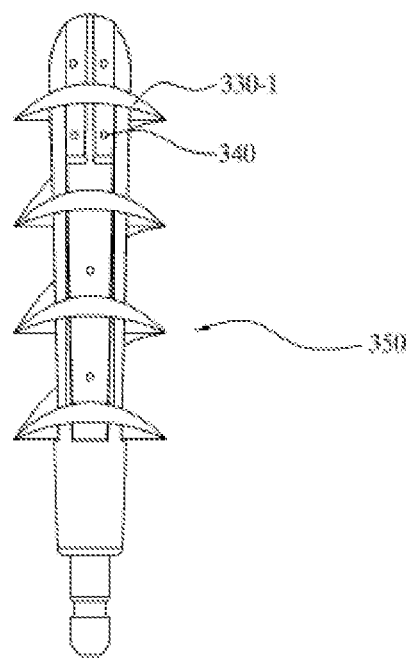
FIG. 4 is a perspective view illustrating a nozzle of the portable functional apparatus for cleaning a vagina according to another exemplary embodiment of the present invention.
Figure 5:
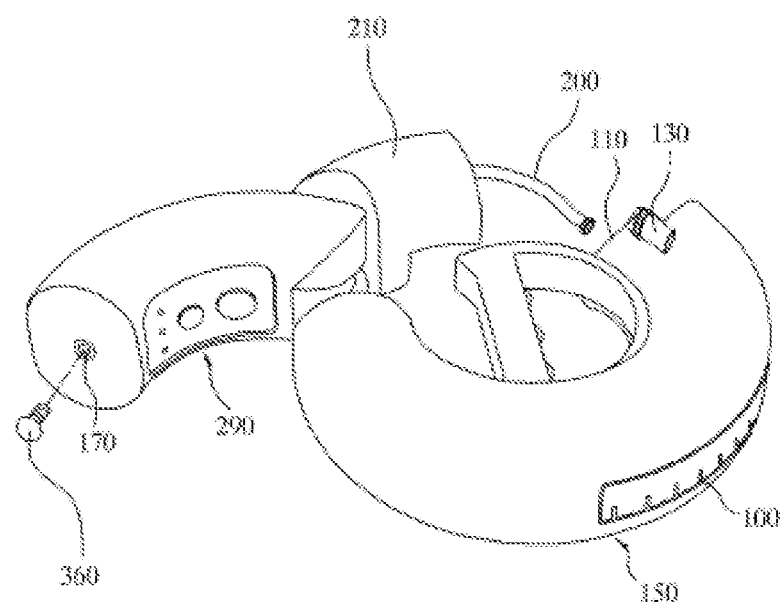
FIG. 5 is a perspective view illustrating a coupling state of the portable functional apparatus for cleaning a vagina according to an exemplary embodiment of the present invention.
Figure 6:
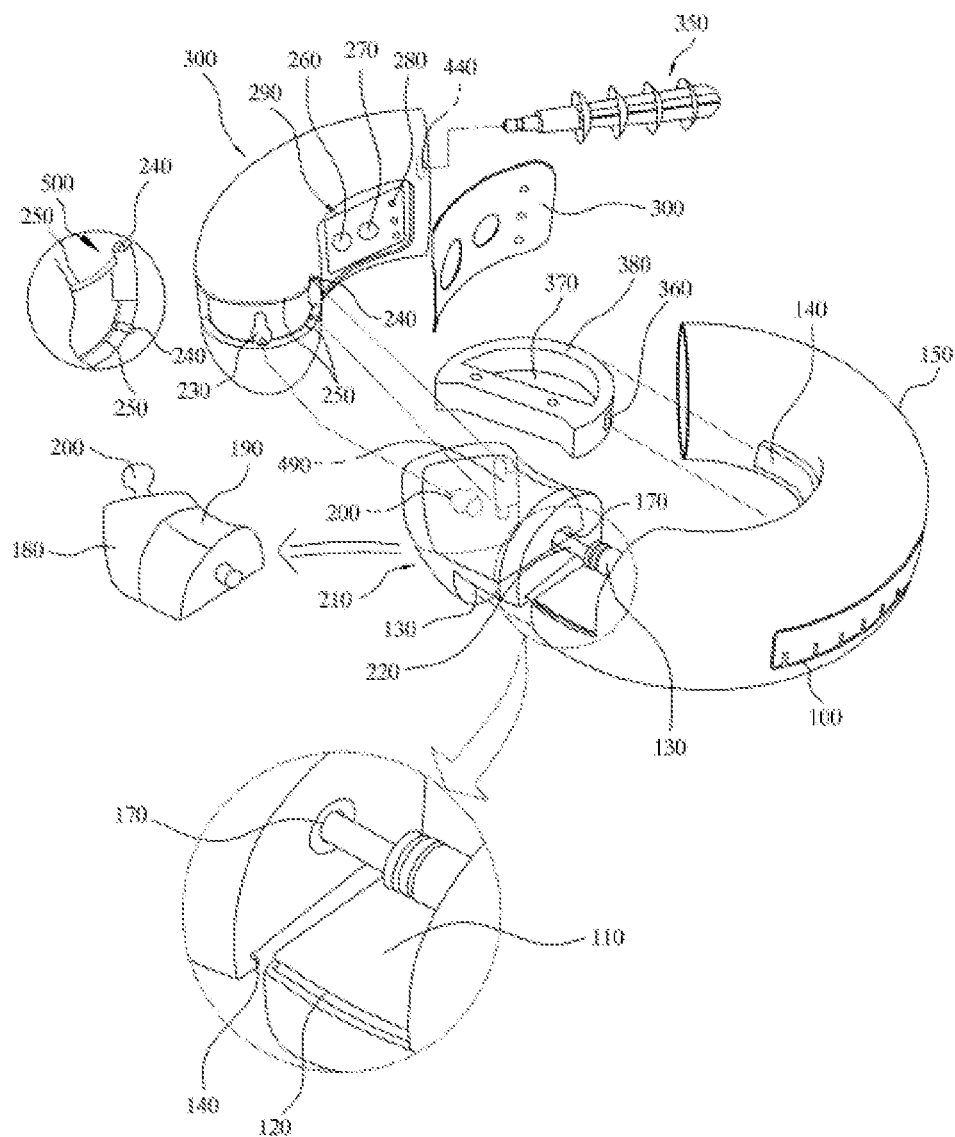
FIG. 6 is an exploded perspective view illustrating the portable functional apparatus for cleaning a vagina according to an exemplary embodiment of the present invention.

The nozzle part 350 is formed therein with a plurality of partitions 330 or a partition 330-1 having a spiral-like shape shown in FIG. 3 or 4. An outlet 320 is formed between the partitions so that a cleaning solution and a foreign material are discharged to the outside. A plurality of exhaust holes 340 are formed between the partitions so that the cleaning solution reaches the secret parts.

Figure 7:
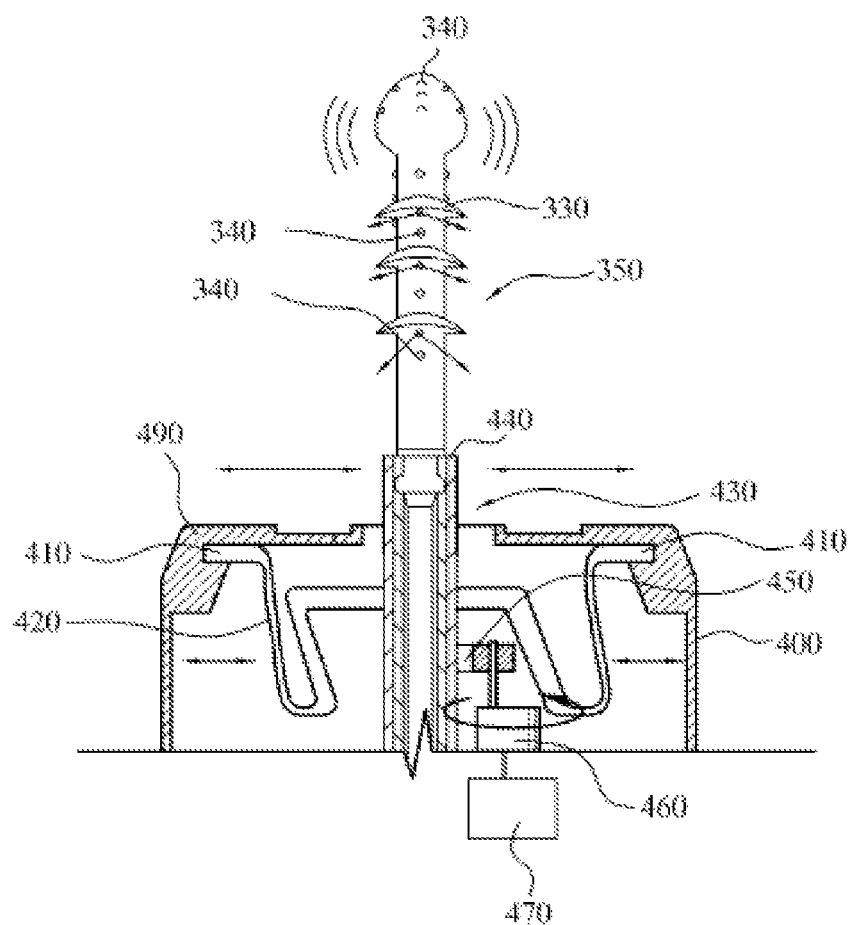
FIG. 7 is a sectional view illustrating the portable functional apparatus for cleaning a vagina according to an exemplary embodiment of the present invention on which a massage device is mounted.

In FIG. 7 according to another embodiment of the present invention, a vibration part is configured to improve a cleaning operation and a massage effect in the vagina.

The support member 430 of the nozzle operation part 300 coupled with the nozzle part 350 is formed therein with the fitting hole 490 inside the case 400. A fitting blade 410 is mounted in the fitting hole 490 to provide vibration.

A vibration part 420 having a curved structure is mounted with the fitting blade 410 formed at fitting holes 490 which are formed at left and right sides of the support member 430. A support member 430 in which a rubber ring is inserted, and the rubber ring is mounted in a center of the vibration part 420. A guide bar 450 and an eccentric shaft 460 connected to the guide bar are mounted so that the support member 430 may be shaken. A motor 470 is configured to rotate the eccentric shaft 460.

If the motor 470 is operated, the eccentric shaft 460 is rotated. If the guide bar 450 connected to the eccentric shaft 460 shakes the vibration part 420 to rotate the vibration part 420 at high speed so that the vibration part 420 rapidly vibrates.

As described above, the vibration occurs and the cleaning solution is supplied through the nozzle part 340 so that cleaning and massage effect due to the vibration may be maximized.

As described above, the cleaning and massage are performed, the nozzle part 350 is removed, and a plug 390 is inserted into and fixed to the nozzle part 350. Next, the nozzle operation part 300 is rotated to locate the body having the donut shape to an original position. As described above, the nozzle operation part 300 is rotated to insert the nozzle part 350 in the vagina so that the controller 290 including an on/off switch 260, a water pressure meter 270, and the operation lamp serving as an operation switch is controlled to adjust water pressure and an operation time.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

The invention claimed is:

1. A portable functional apparatus for cleaning a vagina, comprising:
    a body having a donut shape;
    a water barrel part having a semi-cylindrical shape formed so that the body is separated by units, the water barrel part being separated from the body, and a coupling projection being formed at an inner surface of the water barrel part, a water level indicator part being formed at an outer surface of the water barrel part,
    a handle part formed therein with a coupling groove which is formed at the coupling projection;
    a pumping part coupled with the water barrel part having a semi-cylindrical shape, a hose being inserted into and coupled with an adhesion projection to exhaust a cleaning solution of the water barrel part, and the pumping part being mounted therein with a motor and a pump; and
    a nozzle operation part including a rotating part and a controller, the rotating part coupled with the pumping part to be rotated within a predetermined range, and a controller mounted therein with the rotating part, the controller being formed therein with a fitting projection connected to a connection hose to supply the cleaning solution, the controller being formed therein with an insertion hole, a nozzle part is formed in a front direction of the insertion hole, an on/off switch, a water pressure meter, and an operation lamp being formed at an inner surface of the controller,
    wherein the apparatus has a projected structure inserted into the vagina, the nozzle operation part is rotated so that the nozzle part is mounted to exhaust water.

2. The portable functional apparatus of claim 1, wherein the water barrel part has a semi-transparent structure that allows a user to view the cleaning solution, a positioning projection is formed at a side of the water barrel part, and a slice projection is formed at an upper surface of the positioning projection, and the adhesion projection is formed at an upper portion of the water barrel part so that the hose is inserted into the adhesion projection.

3. The portable functional apparatus of claim 1, wherein the pumping part comprises the motor and the pump so that the cleaning solution of the water barrel part is pumped, the hose and the connection hose are connected to the pump, the pumping part being coupled with.

4. The portable functional apparatus of claim 1, wherein the rotating part is configured so that the nozzle operation part is rotated as an axis representing the pumping part, a T shaped coupling member is formed at the pumping part and is inserted into a fitting groove of the nozzle operation part, and the T shaped coupling member inserted into the fitting groove is coupled to be moved along a locking protrusion.

5. The portable functional apparatus of claim 1, wherein the nozzle part is formed therein with a plurality of partitions or a partition having a spiral-like shape, an outlet is formed between the partitions, and an exhaust hole is formed between the partitions.

6. The portable functional apparatus of claim 1, wherein the nozzle operation part comprises:
    a vibration part having a curved structure mounted with a fitting blade formed at fitting holes which are formed at left and right sides of a support member inside a case;
    the support member wherein a rubber ring is inserted, the rubber ring being mounted in a center of the vibration part;

a guide bar and an eccentric shaft connected to the guide bar are mounted so that the support member is shaken; and a rotation motor configured to rotate the eccentric shaft.

\* \* \* \* \*